US008383800B2

(12) United States Patent
Simpson et al.

(10) Patent No.: US 8,383,800 B2
(45) Date of Patent: Feb. 26, 2013

(54) MKI67 MINI-PROMOTERS

(75) Inventors: Elizabeth M. Simpson, Vancouver (CA); Wyeth W. Wasserman, Vancouver (CA); Robert A. Holt, North Vancouver (CA); Steven J. Jones, Burnaby (CA); Daniel Goldowitz, Memphis, TN (US); Elodie Portales-Casamar, Vancouver (CA); Cletus D'Souza, Vancouver (CA); Vikramjit Chopra, Vancouver (CA)

(73) Assignee: The University of British Columbia (CA)

( * ) Notice: Subject to any disclaimer, the term of this patent is extended or adjusted under 35 U.S.C. 154(b) by 0 days.

(21) Appl. No.: 12/892,730

(22) Filed: Sep. 28, 2010

(65) Prior Publication Data

US 2011/0136235 A1   Jun. 9, 2011

Related U.S. Application Data

(60) Provisional application No. 61/282,018, filed on Dec. 3, 2009.

(51) Int. Cl.
*C12N 5/10* (2006.01)
(52) U.S. Cl. ..................................... 536/23.5; 435/455
(58) Field of Classification Search ............... 536/23.5; 435/455
See application file for complete search history.

(56) References Cited

U.S. PATENT DOCUMENTS

2006/0292695 A1* 12/2006 Clark et al. .................... 435/370
2009/0018031 A1* 1/2009 Trinklein et al. ............... 506/10

OTHER PUBLICATIONS

Jasin; et al., "Targeted transgenesis", PNAS (1996), 93:8804-8808.
Kim; et al., "Activation of subventricular zone stem cells after neuronal injury", Cell Tissue Res (2008), 331:337-345.
Pekcec; et al., "Effect of aging on neurogenesis in the canine brain", Aging Cell (2008), 7:368-374.
Scholzen; et al., "The Ki-67 Protein: From the Known and the Unknown", Journal of Cellular Physiology (2000), 182:311-322.

* cited by examiner

*Primary Examiner* — Marcia S Noble
(74) *Attorney, Agent, or Firm* — Bozicevic, Field & Francis LLP; Pamela J. Sherwood (57) ABSTRACT

Isolated polynucleotides comprising an MKI67 mini-promoter are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The mini-promoter may also be provided in a vector, for example in combination with an expressible sequence. The polynucleotides find use in a method of expressing a sequence of interest, e.g. for identifying or labeling cells, monitoring or tracking the expression of cells, etc.

8 Claims, 5 Drawing Sheets

SEQUENCE LISTING

```
<160> NUMBER OF SEQ ID NOS: 6

<210> SEQ ID NO 1
<211> LENGTH: 1163
<212> TYPE: DNA
<213> ORGANISM: Homo Sapiens

<400> SEQUENCE: 1
aaagtgcggg gattaccggc gtgagccacc gcgtcccgcc tgtttttaat ttttagcagt      60
tttaaatctt ctggcaatga gtaatgttat agtgtcccag atgtttggtc ctttaagaaa     120
aggatagcag gacgggttat ctcggtggga gcgtgttcca cctctgccct ccgccagccg     180
ccctcgccgg ggatgcaccc aggtattttc ctccggatgc gtgagtggct cgcccgcgga     240
```

```
cacgccagcc ccgccccgcg agcccggttt ccccgccccc tccccgccca cgccctgcgc    300
tcccttccta ttggtcccat gccgcgcttt cccgttcaat cgcagcgctt agcgccagaa    360
tttgaatctt cgttttcgtt tgaattgggc gggcgcgccg ggctggaaga aggaagtgga    420
gggctgacgc tgcgggcggg cgggcgggcg ggaggactcg actcggtggg agccgctaga    480
gccgggcgcc cggggacgta gcctgtaggg ccaccgggtc cccgtcagag gcggcggcgg    540
gagcagcggg gactgcaggc cggggtgcag cgaacgcgac cccgcgggct gcggccggt     600 gtgtgcggag cgtggcgggc gcagcttacc gggcggaggt gagcgcggcg ccggctcctc    660
ctgcggcgga ctttgggtgc gacttgacga gcggtggttc gacaagtggc cttgcgggcc    720
ggatcgtccc aggtgagctg cggccgggac tcctgggagc tgtccggggt cgagggctga    780
gccgcgggga ccccccgagc tctgcgggga cgggcagggg acagacgcgc ggcctgggcc    840
cgactcctcc tgggctctgg cgagggcgtc tcggtggaag ctcccaggag gcgcaggcgc    900
tggcgacaac accccagctg ccggactttg gggcgcgggg gctgcggtc ggatcgtcct     960 ggggtccccg ctagctagct gcggtgtgcg cttctgtggc cggggatagg tgaattgggc   1020
acggggccct tcttagctcc tttgctatca gagtaactcg cacctctttt gcagtggaag   1080
agttgtaaat ttgcttctgg ccttccccta cggattatac ctggccttcc cctacggatt   1140
atactcaact tactgtttag aaa                                           1163

<210> SEQ ID NO 2
<211> LENGTH: 3088
<212> TYPE: DNA
<213> ORGANISM: Homo Sapiens

<400> SEQUENCE: 2
caaacccatg tgcgtccccc caatgccccg ccctgcaggc tgctctgtat ggcccaggtc     60
aactgagctt cttcgggacc ctggaaacag agattttcct ttatgaagcc aacggagcat    120
tcacattgat ttactgtttg gcattgaaac taataacttt tggttttaat aatgatgggt    180
tgctgagctc tgaaaagccc tggccttgat ttagctgccg taaaaatgca caactaaaca    240
gccccccacc agttgcctaa gagcaattta tgaaatctcc ttctgtgttt acagaggaaa    300
tcgccttgta ggagtgtcat catgatgaag acaactccag aacagtcatt ttagctgcag    360
ctgcctctca cctgatcgct cccagtctag aattaatgct gccttcaggt tgtaagaggt    420
ttcctgttgc cttcatttca tatccatcac tgagcatcca cagggtcagg aactgccgtg    480
gagaacaaca ataattgat taaggcaaag aaaatgtgta aaacttctca caggtagcac     540
ctgctgtgtg tttaattcca agccatttct ctgagatccc tgttatggta aatgaacaa     600 aacctccaac tcccagagga ggggctggg agtaggcatg gggtctccat cataagaggg     660
gagcccaccc tgcggagggg ttttctaat tacaatcagt ttccccaaca cgctgtcccc    720
aagtctgcct gcatcaaaga gacagctagc aatggagaca cccaactgct cagagccagg    780
ggctgcatcc agctaccgtt ttcattgctc tgaggttatc tgcgtgtgct gatggcctgg    840
agaagccata ggaaaccatc aggatgtaca cgcagcagtg aggatgcagg aatcagggct    900
tcctaggacc gtgcgcatcg tttgggagga gttgggagca tctaaaactg ggaccttcat    960
gcagatttct taaagatgct tctgcgatgt ccagttggat ttgggtctgg aataaggcgt   1020
gccaagtcac aaagctcctg agccacaggg tgtcactcct gatgttctcc ctgagtgggt   1080
gtgttctcag gggtctgggg acaggagctg catccatgaa tcccagctgg aactctgtta   1140
ctagagaatc tgaatacagt cactcgtcaa ctgagcttgt catgtcagtc gccctccctc   1200
```

-continued

| | |
|---|---|
| acagggtgct gtggattcag gtaaatgtct actaatactt ctcattcctg aataaagaaa | 1260 |
| aaaatgtgag gctcaaaggg agagatgagc ttaaagcctc agaaacttgg agttcttcct | 1320 |
| ggggaaaggg ggcctctgaa acacatgcct ccaaaacacc tcagactaca gtatgaggat | 1380 |
| tatagagttt aactaaaatg aaaataaaac aaacaagcaa aactctcaca aaaatgtgaa | 1440 |
| gaataagagg agacaattcc gattacctca atttcccaaa ataaaacaca atttgactag | 1500 |
| aatgtttgat ctgtaaatat gacataaagg agtaacaaac aaaatgggca atgtaaacga | 1560 |
| tcttgcattt tgcaaagaac ttttggaagt attaaacatg taactattag atctttaaaa | 1620 |
| cagagagtat gtaaaaacaa gggaaaacac tagaacacaa atcgaattac cttttatatg | 1680 |
| aaaagctata cttaaaagac acaaggaat acttacatca attttggata atgactattt | 1740 |
| ttaatactct gtgcttttc aaaaacgttt gtttgtaatg ttaaatatgt ttagaggttt | 1800 |
| aatcatcccc aaatgtgctt atttgatgct agcacttctg tgcatcagtt tcttcatata | 1860 |
| caataaagaa attacattag aacctacatc atgtgatgtt caattaaatg gttgtacatg | 1920 |
| tcactaaagt gcggggatta ccggcgtgag ccaccgcgtc ccgcctgttt ttaattttta | 1980 |
| gcagttttaa atcttctggc aatgagtaat gttatagtgt cccagatgtt tggtccttta | 2040 |
| agaaaaggat agcaggacgg gttatctcgg tgggagcgtg ttccacctct gccctccgcc | 2100 |
| agccgccctc gccggggatg cacccaggta ttttcctccg gatgcgtgag tggctcgccc | 2160 |
| gcggacacgc cagccccgcc ccgcgagccc ggtttccccg cccctcccc gcccacgccc | 2220 |
| tgcgctccct tcctattggt cccatgccgc gcttccccgt tcaatcgcag cgcttagcgc | 2280 |
| cagaatttga atcttcgttt tcgtttgaat tgggcgggcg cgccgggctg gaagaaggaa | 2340 |
| gtggagggct gacgctgcgg gcgggcggc gggcggagg actcgactcg gtgggagccg | 2400 |
| ctagagccgg gcgcccgggg acgtagcctg tagggccacc gggtccccgt cagaggcggc | 2460 |
| ggcgggagca gcggggactg caggccgggg tgcagcgaac gcgaccccgc gggctgcggc | 2520 |
| ccggtgtgtg cggagcgtgg cgggcgcagc ttaccgggcg gaggtgagcg cggcgccggc | 2580 |
| tcctcctgcg gcggactttg ggtgcgactt gacgagcggc ggttcgacaa gtggccttgc | 2640 |
| gggccggatc gtcccaggtg agctgcggcc gggactcctg ggagctgtcc ggggtcgagg | 2700 |
| gctgagccgc ggggaccccc cgagctctgc ggggacgggc aggggacaga cgcgcggcct | 2760 |
| gggcccgact cctcctgggc tctggcgagg gcgtctcggt ggaagctccc aggaggcgca | 2820 |
| ggcgctggcg acaacacccc agctgccgga ctttggggcg ccgggggctg cggtcggatc | 2880 |
| gtcctggggt ccccgctagc tagctgcggt gtgcgcttct gtggccgggg ataggtgaat | 2940 |
| tgggcacggg gccttcctta gctcctttgc tatcagagta actcgcacct cttttgcagt | 3000 |
| ggaagagttg taaatttgct tctggccttc ccctacggat tatacctggc cttcccctac | 3060 |
| ggattatact caacttactg tttagaaa | 3088 |

<210> SEQ ID NO 3
<211> LENGTH: 430
<212> TYPE: DNA
<213> ORGANISM: Homo Sapiens

<400> SEQUENCE: 3

| | |
|---|---|
| caaacccatg tgcgtccccc caatgccccg ccctgcaggc tgctctgtat ggcccaggtc | 60 |
| aactgagctt cttcgggacc ctggaaacag agattttcct ttatgaagcc aacggagcat | 120 |
| tcacattgat ttactgtttg gcattgaaac taataacttt tggttttaat aatgatgggt | 180 |
| tgctgagctc tgaaaagccc tggccttgat ttagctgccg taaaaatgca caactaaaca | 240 |

```
gcccccace  agttgcctaa  gagcaattta  tgaaatctcc  ttctgtgttt  acagaggaaa     300
tcgccttgta  ggagtgtcat  catgatgaag  acaactccag  aacagtcatt  ttagctgcag    360
ctgcctctca  cctgatcgct  cccagtctag  aattaatgct  gccttcaggt  tgtaagaggt    420
ttcctgttgc                                                                430

<210> SEQ ID NO 4
<211> LENGTH: 1030
<212> TYPE: DNA
<213> ORGANISM: Homo Sapiens

<400> SEQUENCE: 4
cttcatttca  tatccatcac  tgagcatcca  cagggtcagg  aactgccgtg  gagaacaaca     60
aataattgat  taaggcaaag  aaaatgtgta  aaacttctca  caggtagcac  ctgctgtgtg    120
tttaattcca  agccatttct  ctgagatccc  tgttatggta  aatggaacaa  aacctccaac    180
tcccagagga  gggggctggg  agtaggcatg  gggtctccat  cataagaggg  gagcccaccc    240
tgcggagggg  ttttctaat  tacaatcagt  ttccccaaca  cgctgtcccc  aagtctgcct     300
gcatcaaaga  gacagctagc  aatggagaca  cccaactgct  cagagccagg  ggctgcatcc    360
agctaccgtt  ttcattgctc  tgaggttatc  tgcgtgtgct  gatggcctgg  agaagccata    420
ggaaaccatc  aggatgtaca  cgcagcagtg  aggatgcagg  aatcagggct  tcctaggacc    480
gtgcgcatcg  tttgggagga  gttgggagca  tctaaaactg  gaccttcat  gcagatttct     540 taaagatgct  tctgcgatgt  ccagttggat  ttgggtctgg  aataaggcgt  gccaagtcac    600
aaagctcctg  agccacaggg  tgtcactcct  gatgttctcc  ctgagtgggt  gtgttctcag    660
gggtctgggg  acaggagctg  catccatgaa  tcccagctgg  aactctgtta  ctagagaatc    720
tgaatacagt  cactcgtcaa  ctgagcttgt  catgtcagtc  gccctccctc  acagggtgct    780
gtggattcag  gtaaatgtct  actaatactt  ctcattcctg  aataaagaaa  aaatgtgag    840 gctcaaaggg  agagatgagc  ttaaagcctc  agaaacttgg  agttcttcct  ggggaaaggg    900
ggcctctgaa  acacatgcct  ccaaaacacc  tcagactaca  gtatgaggat  tatagagttt    960
aactaaaatg  aaaataaaac  aaacaagcaa  aactctcaca  aaaatgtgaa  gaataagagg   1020
agacaattcc                                                              1030

<210> SEQ ID NO 5
<211> LENGTH: 465
<212> TYPE: DNA
<213> ORGANISM: Homo Sapiens

<400> SEQUENCE: 5
gattacctca  atttcccaaa  ataaaacaca  atttgactag  aatgtttgat  ctgtaaatat     60
gacataaagg  agtaacaaac  aaaatgggca  atgtaaacga  tcttgcattt  tgcaaagaac    120
ttttggaagt  attaaacatg  taactattag  atctttaaaa  cagagagtat  gtaaaaacaa    180
gggaaaacac  tagaacacaa  atcgaattac  cttttatatg  aaaagctata  cttaaaagac    240 acaaggaat  acttacatca  attttggata  atgactattt  ttaatactct  gtgctttttc     300
aaaaacgttt  gtttgtaatg  ttaaatatgt  ttagaggttt  aatcatcccc  aaatgtgctt    360
atttgatgct  agcacttctg  tgcatcagtt  tcttcatata  caataaagaa  attacattag    420
aacctacatc  atgtgatgtt  caattaaatg  gttgtacatg  tcact                    465

<210> SEQ ID NO 6
<211> LENGTH: 1163
```

```
<212> TYPE: DNA
<213> ORGANISM: Homo Sapiens

<400> SEQUENCE: 6
aaagtgcggg gattaccggc gtgagccacc gcgtcccgcc tgtttttaat ttttagcagt      60
tttaaatctt ctggcaatga gtaatgttat agtgtcccag atgtttggtc ctttaagaaa    120
aggatagcag gacgggttat ctcggtggga gcgtgttcca cctctgccct ccgccagccg    180
ccctcgccgg ggatgcaccc aggtattttc ctccggatgc gtgagtggct cgcccgcgga    240
cacgccagcc ccgccccgcg agcccggttt ccccgccccc tccccgccca cgccctgcgc    300
tcccttccta ttggtcccat gccgcgcttt cccgttcaat cgcagcgctt agcgccagaa    360
tttgaatctt cgttttcgtt tgaattgggc gggcgcgccg ggctggaaga aggaagtgga    420
gggctgacgc tgcgggcggg cgggcgggcg ggaggactcg actcggtggg agccgctaga    480
gccgggcgcc cggggacgta gcctgtaggg ccaccgggtc cccgtcagag gcggcggcgg    540
gagcagcggg gactgcaggc cggggtgcag cgaacgcgac cccgcgggct gcggcccggt    600
gtgtgcggag cgtggcgggc gcagcttacc gggcggaggt gagcgcggcg ccggctcctc    660
ctgcggcgga ctttgggtgc gacttgacga gcggtggttc gacaagtggc cttgcgggcc    720
ggatcgtccc aggtgagctg cggccgggac tcctgggagc tgtccggggt cgagggctga    780
gccgcgggga cccccgagc tctgcgggga cgggcagggg acagacgcgc ggcctgggcc    840
cgactcctcc tgggctctgg cgagggcgtc tcggtggaag ctcccaggag gcgcaggcgc    900
tggcgacaac accccagctg ccggactttg gggcgcggg ggctgcggtc ggatcgtcct    960
ggggtccccg ctagctagct gcggtgtgcg cttctgtggc cggggatagg tgaattgggc   1020 acggggcct tcttagctcc tttgctatca gagtaactcg cacctctttt gcagtggaag   1080
agttgtaaat ttgcttctgg ccttcccta cggattatac ctggccttcc cctacggatt   1140
atactcaact tactgtttag aaa                                           1163
```

MKI67 MINI-PROMOTERS

CROSS-REFERENCE TO RELATED APPLICATIONS

Pursuant to 35 U.S.C. §119 (e), this application claims priority to the filing date of U.S. Provisional Patent Application Ser. No. 61/282,018 filed Dec. 3, 2009, the disclosure of which application is herein incorporated by reference.

FIELD OF THE INVENTION

The invention relates to gene promoters and regulatory elements. More specifically, the invention relates to novel MKI67 promoter compositions and related methods.

BACKGROUND

MKI67, alternately referred to as Ki-67 and Ki-67 antigen, is an endogenous marker for cellular proliferation and a traditional marker of neurogenesis. MKI67 is present in the nuclei of dividing cells during the $G_1$, S, and $G_2$ phases of mitosis, however it is not found in significant amounts in resting or $G_0$ phases. Because MKI67 protein is found in most proliferating cells, including tumor cells, it has become well-established marker for the growth function of a given cell. For instance, the fraction of Ki-67-positive tumor cells is often correlated with the clinical progression of different cancers, such as prostate or breast cancers. The 'growth factor' or 'Ki-67 index' of a population of cells, for instance tumor cells, may be utilized for various purposes, for instance for prognostication of tumor development, or for determination of appropriate therapeutic strategies for a given proliferative disease such as cancer (Scholzen and Gerdes 2000).

MKI67 has been used in various studies as a marker for neurogenesis in the brain. For instance, MKI67 was measured alongside doublecortin (DCX), a marker for early or new neural progenitor cells, to study hippocampal neurogenesis and neuronal migration in various mouse strains (Kim et al., 2008). In another study, MKI67 was again measured alongside DCX to investigate the potential decline in neurogenesis in adult dogs (Pekcec et al. 2008). These studies highlight the utility of MKI67 in the study of neurogenesis.

Minimal human promoter elements which are capable of driving expression in specific cell types and/or in specific regions of the brain are of interest. Also of interest is the identification of minimal elements required for adequate expression and specificity that allow ease of use in expression constructs.

RELEVANT LITERATURE

References of interest include:
Jasin, M., M. E. Moynahan, et al. (1996) "Targeted transgenesis." Proc Natl Acad Sci U S A 93(17): 8804-8;
Kim Y., Szele F. G., (2008) "Activation of subventricular zone stem cells after neuronal injury." Cell and Tissue Research 331(1): 337-345;
Pekcec, A., W. Baumgartner, et al. (2008) "Effect of aging on neurogenesis in the canine brain." Aging Cell 7(3): 368-74; and
Scholzen, T. and J. Gerdes (2000) "The Ki-67 protein: from the known and the unknown." J Cell Physiol 182(3): 311-22.

SUMMARY OF THE INVENTION

The present invention provides novel nucleic acid compositions and methods relating to MKI67 promoters having a sequence other than a native MKI67 promoter.

In one embodiment of the invention, there is provided an isolated nucleic acid fragment comprising an MKI67 mini-promoter, wherein the MKI67 mini-promoter comprises one or more MKI67 regulatory elements operably linked in a non-native conformation to an MKI67 basal promoter. In other embodiments, there is provided an isolated nucleic acid fragment comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. The MKI67 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising an MKI67 mini-promoter element, wherein the MKI67 mini-promoter comprises one or more MKI67 regulatory elements operably linked in a non-native conformation to an MKI67 basal promoter. In other embodiments, there is provided an expression vector comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. The MKI67 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell a expression vector comprising an MKI67 mini-promoter element, wherein the MKI67 mini-promoter comprises one or more MKI67 regulatory elements operably linked in a non-native conformation to an MKI67 basal promoter. In other embodiments, there is provided a method for expressing a gene, protein, RNA interference molecule or the like in a cell, the method comprising introducing into the cell an expression vector comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. Cells of interest may include proliferating cells or proliferating neurons. The MKI67 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising an MKI67 mini-promoter element operably linked to an expressible sequence, wherein the MKI67 mini-promoter element comprises one or more MKI67 regulatory elements operably linked in a non-native conformation to an MKI67 basal promoter element, and wherein the expressible sequence comprises a reporter gene. In another embodiment, the MKI67 mini-promoter element comprises an MKI67 basal promoter element. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. In some embodiments, the cell is a neuronal cell. In other embodiments, the cell is a proliferative cell, for instance a cancer cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising an MKI67 mini-promoter element operably linked to an expressible sequence, wherein the MKI67 mini-promoter element comprises one or more MKI67 regulatory elements operably linked in a non-native conformation to an MKI67 basal promoter element, and wherein the expressible sequence comprises a reporter gene; and 2) detecting the expression of the reporter gene in the progeny of the cell as a means of determining the lineage, identity or developmental state of the progenitor cell or progeny thereof. In other embodiments, the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. In some embodiments, the cell is a neuronal cell. In other embodiments, the cell is a proliferative cell, for instance a cancer cell.

DETAILED DESCRIPTION

Compositions that include novel polynucleotides comprising MKI67 promoter elements (also referred to herein as MKI67 mini-promoters) as well as novel expression vectors comprising said MKI67 promoter elements (or mini-promoters), are provided. Also provided are various methods utilizing the subject MKI67 promoter (or mini-promoter) elements or expression vectors.

The term 'MKI67' refers to the gene which encodes the MKI67 protein, also referred to as Ki-67, Ki-67 antigen and Ki-67 protein. The human homolog of MKI67 is encoded by the human gene identified as EntrezGene #4288. The protein encoded by human MKI67 has the Protein Accession #P46013.2 (Swiss-Prot). Other mammalian MKI67 homologs include but are not limited to: *Rattus norvegicus* (EntrezGene #291234), *Mus musculus* (EntrezGene #17345). The MKI67 protein has been shown to be associated with cellular proliferation, and has been used as a marker of such in numerous cell types, including neuronal cells.

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. An 'MKI67 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 6, and which comprises at least 2, usually at least 4, and most usually at least 6 of the identified conserved sequences listed in Table 1.

TABLE 1

List of conserved sequences in the human MKI67 basal promoter - SEQ ID NO: 6. The start and end coordinates of the suences are relative to the full SEQ ID NO: 6 sequence.

| Start (relative to SEQ ID NO: 2/6) | End (relative to SEQ ID NO: 2/6) | Invariant sequence type |
|---|---|---|
| 64 | 88 | Conserved sequence |
| 144 | 167 | Conserved sequence |
| 331 | 394 | Conserved sequence |
| 627 | 732 | Exon (5'UTR) |
| 732 | 751 | Conserved sequence |
| 1075 | 1163 | Exon (5'UTR) |

A promoter may also include one or more 'regulatory elements' which may also influence the expression or transcription by the promoter. Such regulatory elements encode specific DNA sequences which bind other factors, which may include but are not limited to enhancers, silencers, insulators, and/or boundary elements. An 'MKI67 regulatory element', in the context of the present invention and as used herein, may be a nucleic acid compound having a sequence with at least 65%, at least 70%, at least 80%, at least 85%, at least 90%, at least 95%, or at least 99% similarity to SEQ ID NO: 3, 4, or 5. In the context of MKI67 regulatory element #1 (SEQ ID NO: 3), an MKI regulatory element may be a nucleic acid sequence which also contains at least 1, usually at least 2, and most usually at least 3 of the identified conserved sequences listed in Table 2. In the context of MKI67 regulatory element #2 (SEQ ID NO: 4), an MKI regulatory element may be a nucleic acid sequence which also contains at least 6, usually at least 8, and most usually at least 11 of the identified conserved sequences listed in Table 3. In the context of MKI67 regulatory element #3 (SEQ ID NO: 5), an MKI regulatory element may be a nucleic acid sequence which also contains at least 2, usually at least 3, and most usually at least 4 of the identified conserved sequences listed in Table 2. The present invention provides, in certain embodiments as described herein, different promoters of the MKI67 gene. In some embodiments, the MKI67 promoter comprises one or more MKI67 regulatory elements operably linked to an MKI67 basal promoter. In certain embodiments, the MKI67 regulatory elements are directly joined with no intervening sequences. In other embodiments, the MKI67 regulatory elements may be operably linked with intervening sequences. In general the spacing between the regulatory elements is not more than about 15 KB, generally not more than about 10 KB, usually not more than about 1 KB, more often not more than about 500 nt, and may be not more than about 100 nt, down to a direct joining of the two sequences.

TABLE 2

List of conserved sequences in the human MKI67 regulatory region #1 - SEQ ID NO: 3. The start and end coordinates of the sequences are relative to the full SEQ ID NO: 3 sequence.

| Start (relative to SEQ ID NO: 3) | End (relative to SEQ ID NO: 3) | Invariant sequence type |
|---|---|---|
| 92 | 339 | Conserved sequence |
| 345 | 367 | Conserved sequence |
| 383 | 414 | Conserved sequence |

TABLE 3

List of conserved sequences in the human MKI67 regulatory region #2 - SEQ ID NO: 4. The start and end coordinates of the sequences are relative to the full SEQ ID NO: 4 sequence.

| Start (relative to SEQ ID NO: 4) | End (relative to SEQ ID NO: 4) | Invariant sequence type |
|---|---|---|
| 22 | 121 | Conserved sequence |
| 144 | 197 | Conserved sequence |
| 220 | 263 | Conserved sequence |
| 283 | 317 | Conserved sequence |
| 334 | 380 | Conserved sequence |
| 394 | 428 | Conserved sequence |
| 481 | 502 | Conserved sequence |
| 731 | 774 | Conserved sequence |
| 779 | 806 | Conserved sequence |
| 816 | 835 | Conserved sequence |
| 851 | 900 | Conserved sequence |

TABLE 4

List of conserved sequences in the human MKI67 regulatory region #3 - SEQ ID NO: 5. The start and end coordinates of the sequences are relative to the full SEQ ID NO: 5 sequence.

| Start (relative to SEQ ID NO: 5) | End (relative to SEQ ID NO: 5) | Invariant sequence type |
|---|---|---|
| 1 | 56 | Conserved sequence |
| 124 | 150 | Conserved sequence |
| 177 | 246 | Conserved sequence |
| 337 | 365 | Conserved sequence |

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene between the identified elements may be partially or completely removed. Other non-native sequences may optionally be inserted between the identified promoter elements. The term mini-promoter may also refer to a minimal promoter element in a native conformation which is capable of driving protein expression, but which has had non-essential elements removed in order to reduce its size. A mini-promoter may provide certain advantages over larger promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters would be apparent to one of skill in the art. In some embodiments of the invention, there are thus provided novel MKI67 mini-promoters comprising one or more MKI67 regulatory elements operably linked in a non-native conformation to an MKI67 basal promoter. In general the spacing between the one or more MKI67 regulatory elements and the MKI67 basal promoter is not more than about 15 KB, generally not more than about 10 KB, usually not more than about 1 KB, more often not more than about 500 nt, and may be not more than about 100 nt, down to a direct joining of the two sequences. In other embodiments, there are provided novel MKI67 mini-promoters comprising an MKI67 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and/or regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which is may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

MKI67 Promoters

The present invention herein provides novel MKI67 mini-promoter sequences which are capable of effecting transcriptional expression in a spatial and temporal fashion which may be similar to naturally occurring MKI67 promoters, although the invention may also provide for variation away from the native expression patterns. In some embodiments, the MKI67 mini-promoters of the invention comprise MKI67 promoter elements joined in a non-native configuration, thus providing advantageous characteristics. In other embodiments, the MKI67 mini-promoters comprise basal promoters with advantageous characteristics. Also provided are novel expression vector compositions comprising MKI67 mini-promoters which allow consistent specific spatiotemporal transcription of expression sequences. Also provided are novel methods utilizing these MKI67 mini-promoters and expression vectors.

The MKI67 mini-promoters of some embodiments of the invention, as described herein, comprise MKI67 promoter elements that are joined by non-native sequences. In this context, the native intervening sequences may have been partially or completely removed, and optionally may have been replaced with non-native sequences. In such a fashion, the natural spacing of the promoter elements, for instance the human MKI67 regulatory elements corresponding to SEQ ID NO: 3, SEQ ID NO: 4 and/or SEQ ID NO: 5 and the human MKI67 basal promoter element corresponding to SEQ ID NO: 6, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications. The MKI67 mini-promoters of other embodiments of the invention comprise MKI67 basal promoters. The advantage of such basal promoters are also related to the significantly reduced size as compared to native promoters.

In certain embodiments, human MKI67 mini-promoters having a sequences corresponding to SEQ ID NO: 1 and 2 direct expression of an expressible sequence which is operably linked downstream of the MKI67 promoter in specific cell types in different regions of the brain (see e.g., the non-limiting working examples). The MKI67 regulatory elements (SEQ ID NOs: 3, 4, 5) and MKI67 basal promoter element (SEQ ID NO: 6) have sequences which are identical to those found upstream of the human MKI67 gene.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified mini-promoter provide for a transcription rate of an expressible sequence operably linked to a modified promoter sequence that is at least about 75% the transcription rate of the promoter sequence of SEQ ID NO:1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. Applicants have identified 24 conserved sequences in one of the MKI67 promoters of the invention (SEQ ID NO: 1), as shown in Table 5, where 3 such conserved sequences are present in regulatory element #1 (SEQ ID NO: 3), 11 conserved sequences are present in regulatory element #2 (SEQ ID NO: 4), 4 conserved elements are present in regulatory element #3 (SEQ ID NO: 5), and 6 conserved elements are present in regulatory element #1. A promoter of interest in the present invention may comprise at least 15, usually at least 20, and may comprise all 24 of the identified conserved sequences. Alternately, for promoters of interest comprising only the basal promoter (SEQ ID NO: 2 or 6), the inventors have identified 6 conserved elements (Table 1). A promoter of interest may comprise at least 2, usually at least 4, and most usually at least 6 of the conserved elements from Table 1. The spacing of conserved sequences may be the same as the native spacing, or it may be different than the native spacing. The order of the conserved sequences may be the same as the native order or the sequences may be rearranged. Sequences set forth in SEQ ID NO:1 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

TABLE 6

List of conserved sequences in the human MKI67 mini-promoter of certain embodiments of the invention - SEQ ID NO: 1. The start and end coordinates of the sequences are relative to the full SEQ ID NO: 1 sequence.

| Start (relative to SEQ ID NO: 1) | End (relative to SEQ ID NO: 1) | Invariant sequence type |
|---|---|---|
| 92 | 339 | Conserved sequence |
| 345 | 367 | Conserved sequence |
| 383 | 414 | Conserved sequence |
| 452 | 551 | Conserved sequence |
| 574 | 627 | Conserved sequence |
| 650 | 693 | Conserved sequence |
| 713 | 747 | Conserved sequence |
| 764 | 810 | Conserved sequence |
| 824 | 858 | Conserved sequence |
| 911 | 932 | Conserved sequence |
| 1161 | 1204 | Conserved sequence |
| 1209 | 1236 | Conserved sequence |
| 1246 | 1265 | Conserved sequence |
| 1281 | 1330 | Conserved sequence |
| 1461 | 1516 | Conserved sequence |
| 1584 | 1610 | Conserved sequence |
| 1637 | 1706 | Conserved sequence |
| 1797 | 1825 | Conserved sequence |
| 1989 | 2013 | Conserved sequence |
| 2069 | 2092 | Conserved sequence |
| 2256 | 2319 | Conserved sequence |
| 2552 | 2657 | Exon (5' UTR) |
| 2657 | 2676 | Conserved sequence |
| 3000 | 3088 | Exon (5' UTR) |

In one embodiment of the invention, there is provided an isolated nucleic acid fragment comprising an MKI67 mini-promoter, wherein the MKI67 mini-promoter comprises one or more MKI67 regulatory elements operably linked in a non-native conformation to an MKI67 basal promoter. In other embodiments, there is provided an isolated nucleic acid fragment comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. The MKI67 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

Means of expressing a gene, protein, RNA interference molecule or the like in a cell, tissue or organ, are provided, utilizing the subject expression vectors comprising MKI67 mini-promoters. In one embodiment, there is provided an expression vector comprising an MKI67 mini-promoter element, wherein the MKI67 mini-promoter comprises one or more MKI67 regulatory elements operably linked in a non-native conformation to an MKI67 basal promoter. In other embodiments, there is provided an expression vector comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. The MKI67 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In certain embodiments, the subject expression vectors comprising novel MKI67 mini-promoter elements are capable of directing transcription of an expression sequence in specific cell types in specific regions of the brain and body, most notably surrounding the ventricles, in the rostral migratory stream and dentate gyrus, all regions that are associated with neurogenesis. In some embodiments of the invention, there is thus provided a method for expressing a gene, protein, RNA interference molecule or the like in the targeted cells of the brain. In one embodiment, there is provided a method for expressing a gene, protein, RNA interference molecule or the like in a cell, the method comprising introducing into the cell a expression vector comprising an MKI67 mini-promoter element, wherein the MKI67 mini-promoter comprises one or more MKI67 regulatory elements operably linked in a non-native conformation to an MKI67 basal promoter. In other embodiments, there is provided a method for expressing a gene, protein, RNA interference molecule or the like in a cell, the method comprising introducing into the cell an expression vector comprising an MKI67 mini-promoter, wherein the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. Cells of interest may include neurons, proliferating neurons, or other proliferative cell types, for instance cancer cells. The MKI67 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising an MKI67 mini-promoter element operably linked to an expressible sequence, wherein the MKI67 mini-promoter element comprises one or more MKI67 regulatory elements operably linked in a non-native conformation to an MKI67 basal promoter element, and wherein the expressible sequence comprises a reporter gene. In another embodiment, the MKI67 mini-promoter element comprises an MKI67 basal promoter element. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. In some embodiments, the cell may be a neuron, a proliferating neuron, or another proliferative cell type, for instance a cancer cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising an MKI67 mini-promoter element operably linked to an expressible sequence, wherein the MKI67 mini-promoter element comprises one or more MKI67 regulatory elements operably linked in a non-native conformation to an MKI67 basal promoter element, and wherein the expressible sequence comprises a reporter gene; and 2) detecting the expression of the reporter gene in the progeny of the cell as a means of determining the lineage, identity or developmental state of the progenitor cell or progeny thereof. In other embodiments, the MKI67 mini-promoter comprises an MKI67 basal promoter. The MKI67 mini-promoter may have a nucleic acid sequence which is substantially similar in sequence and function to SEQ ID NO: 1 or 2. The one or more MKI67 regulatory elements may have nucleic acid sequences which are substantially similar in sequence and function to SEQ ID NO: 3, SEQ ID NO: 4, and/or SEQ ID NO: 5. The MKI67 basal promoter may have a nucleic acid sequence which is substantially similar in sequence and function to SEQ ID NO: 6. In some embodiments, the cell may be a neuron, a proliferating neuron, or another proliferative cell type, for instance a cancer cell.

The inventors herein further describe the present invention by way of the following non-limiting examples:

WORKING EXAMPLES

General Methods

Expression Vector

Figure 1:
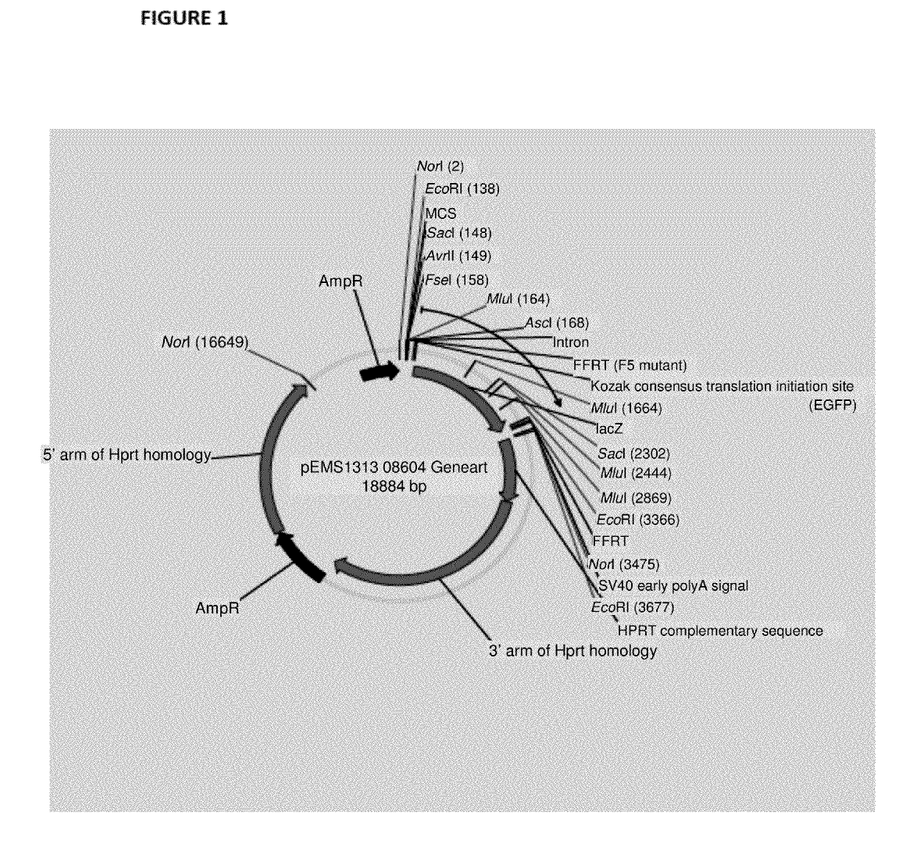
FIG. 1: Vector diagram of backbone pEMS1313

The nucleic acid fragment corresponding to SEQ ID NO: 1 or 2 was inserted into the multiple cloning site of the pEMS1313 (see FIG. 1) to produce the expression vectors used in the experiments.

Derivation of mEMS 1202 Embryonic Stem Cells

Blastocysts were obtained from natural mating of B6-Hprt1$^{b-m3}$ homozygous females to 129-ROSA26 heterozygous males at 3.5 dpc. Blastocysts were flushed from uterine horns as per (Hogan et al. 1994), cultured in Embryo-Max® KSOM with ½ Amino Acids, Glucose and Phenol Red (Cat # MR-121, Millipore/Chemicon, Temecula, Calif.) for 3-5 h, and then transferred onto mitomycin C (mitC; Cat#M4287, Sigma, Oakville, ON) mitotically inactivated B6-Hpa$^{1b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well developed ICM (inner cell mass) were treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON), 1000 U ESGRO-LIF (Millipore, ESG1107) and 0.01% β-mercaptoethanol (Sigma, Oakville, ON)) in 25%, 50%, 75% proportions (respectively) to adapt the cells to FBS containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sor$^{tm1Sor}$ and WT alleles and Hprt1$^{b-m3}$ and WT alleles. B6129F1-Gt(ROSA)26Sor$^{tm1sor}$/+, Hprt1$^{b-m3}$/Y (mEMS1204 series) and B6129F1-Gt(ROSA)26Sor$^{tm1sor}$+/+, Hprt1$^{b-m3}$/Y (mEMS1202 series) cell lines were identified.

Knock-in at the Hprt1 Locus

The MKI67 expression vector plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. mEMS1202 ESCs were grown to confluence on 4-6 T75 flasks of mitC treated Hprt1$^{b-m3}$ mouse embryonic feeders (MEFs) in FBS-ESC media. ESCs (1.7–2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3$^{rd}$ day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of Knock-in Mice

Chimeric mice from targeted ESCs were generated by microinjection (Hogan et al. 1994) into E3.5 blastocysts followed by implantation into the uterine horns of 2.5 day pseudopregnant ICR females. Chimeras were identified and coat color chimerism determined as outlined below.

Male chimeras derived from the mEMS1202 cell lines were mated with B6-Alb females, and germline transmission identified by the presence of the dominant Tyr$^+$ (tyrosinase; wild type) and the A$^w$ (nonagouti; white bellied agouti) or a (nonagouti; nonagouti) alleles making the progeny appear brown with a cream belly or black, respectively. Non-germline progeny were homozygous for the recessive Tyr$^{c-2J}$ (tyrosinase; albino 2 Jackson) allele and appear white. All germline female offspring should carry the knock-in X Chromosome and were mated with B6 males. N2 offspring were analyzed for the presence of the KI allele by PCR.

Determination of Coat Color Chimerism mEMS1202-derived chimeras were identified and level of coat color chimerism determined as follows. mEMS1202 ESCs, heterozygous A$^w$/a and homozygous for the wild type Tyr$^+$ alleles will produce chimeras with agouti and black patches on a white background when injected into B6-Alb blastocysts. The agouti patches result from melanocytes derived solely from the ESCs (A$^w$/a, Tyr$^+$/Tyr$^+$), whereas 'black' patches result from melanocytes that are a mixture of ESC (A$^w$/a, Tyr$^+$/Tyr$^+$) and host (a/a, Tyr$^{c-2J}$/Tyr$^{c-2J}$). For E14TG2a injections into B6 and mEMS1202 injections into B6-Alb, overall chimerism was calculated by summing the percent of coat color patches derived solely from the ESC, plus half the percent of the ESC+host areas, where we conservatively estimated that half the melanocytes derive from the ESC and half from the host.

Reporter Gene Detection

Adult male chimeric and age matched control mice were perfused with 4% paraformaldehyde (PFA) as previously described (Young et al. 2002). Whole brains were dissected out and post-perfusion immersion fixed with PFA for 2 hours at 4° C. Brains were then transferred to 25% sucrose at 4° C. overnight with gentle shaking. The brains were cryostat sectioned sagittally at 1 mm and sections were mounted in 12-well tissue culture plates. LacZ expression was detected by using 5-bromo-4-chloro-3-indolyl β-d-galactopyranoside (x-Gal) as the substrate. The x-Gal staining solution contained the following chemicals: 1.0 mg/ml X-Gal, 2 mM potassium ferricyanide, 2 mM, potassium ferrocyanide, and 40 mM MgCl$_2$ in PBS. In brief, slide mounted brain sections are rinsed with phosphate buffered saline (PBS), then incubate with x-Gal (Boeringer Mannheim, Indianapolis, Ind.) at 37° C. from two hours to overnight. After the plates were taken out of the incubator they were rinsed with PBS and moved into PBS for storage. Bright field images were visualized on a Leica MZ125 dissecting microscope and photographed with an Olympus Coolsnap cf color camera.

Example 1

Selection of MKI67 Promoter Elements

Under the assumption that sequences under selective pressure will be more conserved than those that are not, cross-species comparisons, or phylogenetic footprinting, were utilized to identify regulatory regions. The two mammalian species with a desirable evolutionary distance to use for this approach are human and mouse. In the specific case of MKI67, the conservation level between human and mouse was computed taking into consideration the non-coding sequence surrounding the MKI67 gene. For this genomic region including a lot of non-coding sequences conserved down to the frog, a threshold of 70% of identity was set up to select our candidate regulatory regions. The MKI67 basal promoter (SEQ ID NO: 6) and three upstream regulatory regions (SEQ ID NOs: 3, 4, 5) were chosen based on these criteria.

Example 2

Expression of Reporter by MKI67 Promoter Elements

Figure 2:
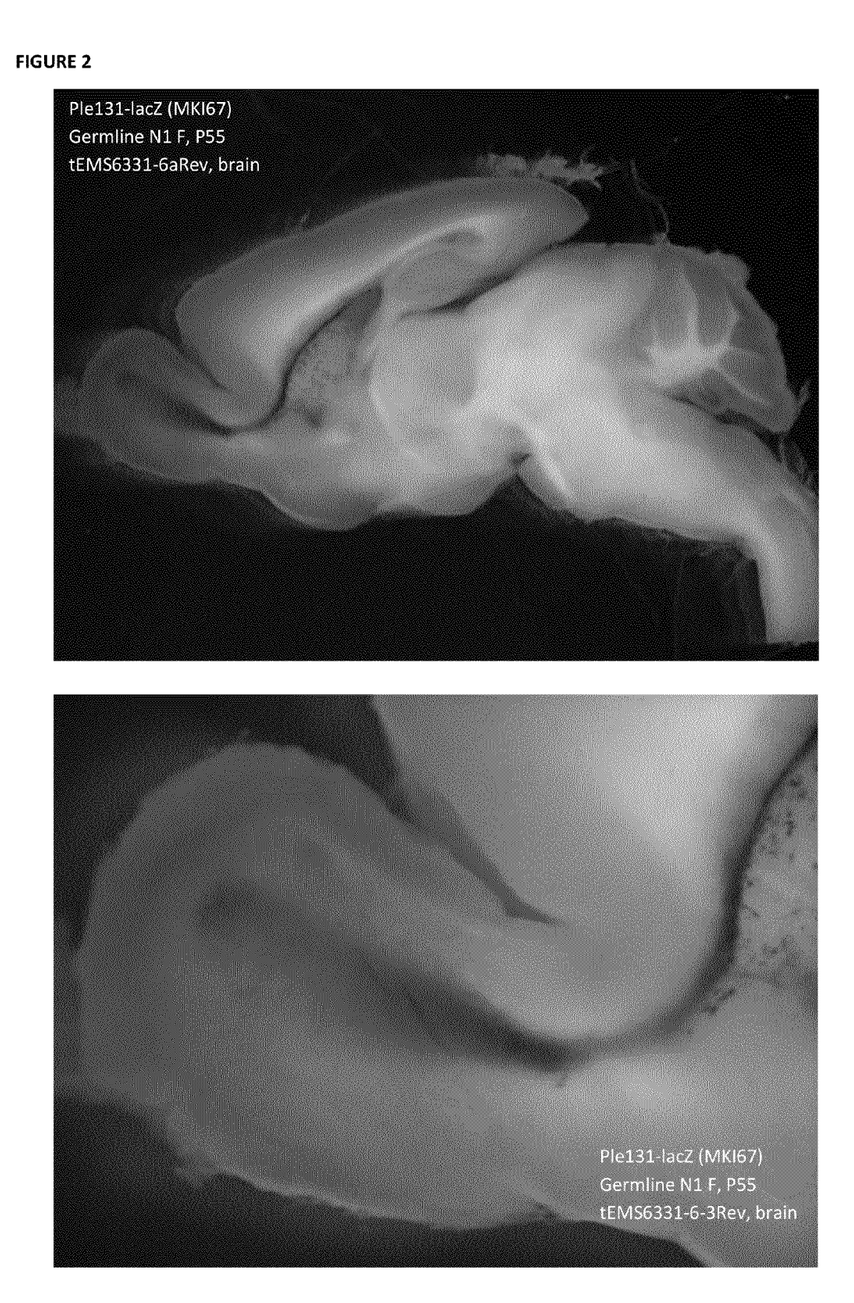
FIG. 2: Expression of reporter driven by MKI67 mini-promoter, in rostral migratory stream region of the mouse brain. Dark regions indicate expression of the lacZ reporter gene from the MKI67 mini-promoter. The lower photographs are a higher magnification from the upper image.
Figure 3:
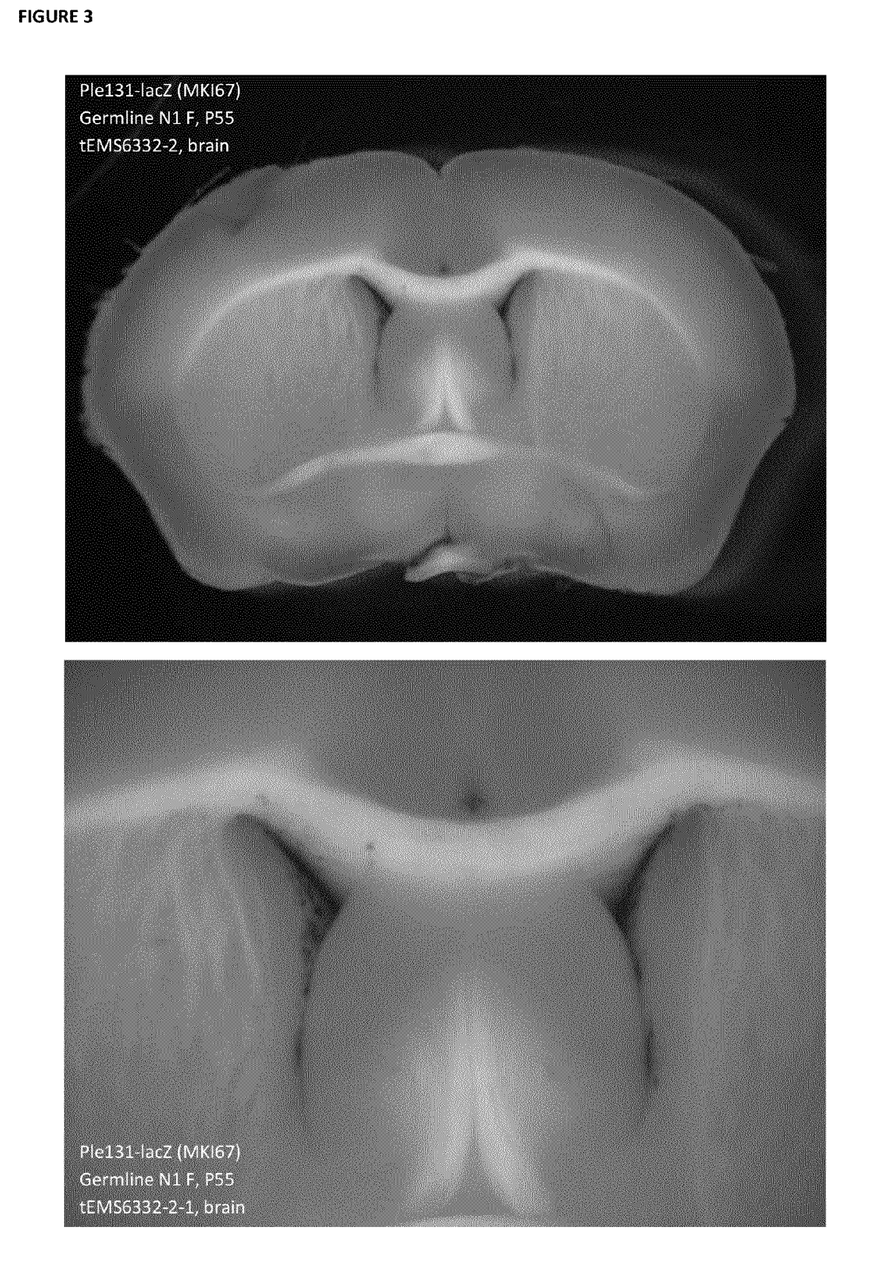
FIG. 3: Expression of reporter driven by MKI67 mini-promoter, in the region surrounding the ventricles of the mouse brain. Dark regions indicate expression of the lacZ reporter gene from the MKI67 mini-promoter. The lower photograph is a higher magnification from the upper image.
Figure 4:
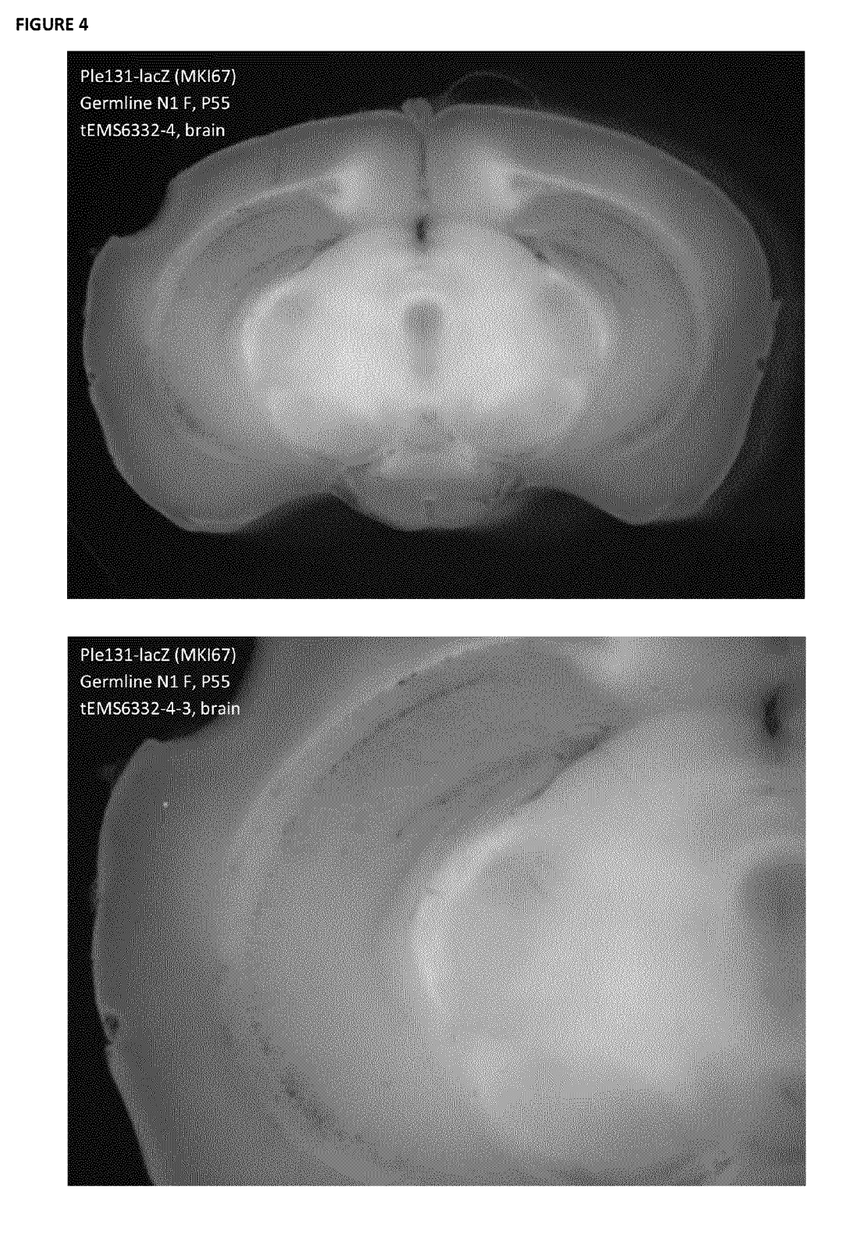
FIG. 4: Expression of reporter driven by MKI67 mini-promoter, in the hippocampal CA1 and dentate gyrus regions of the mouse brain. Dark regions indicate expression of the lacZ reporter gene from the MKI67 mini-promoter. The lower photograph is a higher magnification from the upper image.

The MKI67 DNA expression vectors comprising the MKI67 promoter element corresponding to SEQ ID NO: 2 (regulatory regions corresponding to SEQ ID NO: 3, 4, and 5 fused to basal promoter SEQ ID NO: 6) was introduced into mouse embryonic stem cells (ESCs) at the HPRT locus. The ESCs were used to generate genetically modified mice containing MKI67 mini-promoters. Immunohistochemical analysis of mouse brain tissue slices revealed expression surrounding the ventricles, in the rostral migratory stream, and in the hippocampal CA1 and dentate gyrus. FIG. 2 shows expression from the MKI67 mini-promoter (SEQ ID NO: 2) in the rostral migratory region of the mouse brain. FIG. 3 shows expression from the MKI67 mini-promoter (SEQ ID NO: 2) in the region surrounding the ventricles of the brain. FIG. 4 shows expression from the MKI67 mini-promoter (SEQ ID NO: 2) in the hippocampal CA1 and dentate gyrus region of the brain.

Sequence Descriptions
SEQ ID NO: 1, human MKI67 mini-promoter element, basal promoter element only (1163 bp);
SEQ ID NO: 2, human CLDN 5 mini-promoter–basal promoter+regulatory elements 1, 2 and 3 (3088 bp);
SEQ ID NO: 3, human MKI67 regulatory element 1: 430 bp;
SEQ ID NO: 4, human MKI67 regulatory element 2: 1030 bp;
SEQ ID NO: 5, human MKI67 regulatory element 3: 465 bp (reverse orientation from natural sequence); and
SEQ ID NO: 6, human MKI67 basal promoter element: 1163 bp.

REFERENCES

Bronson, S. K., E. G. Plaehn, et al. (1996). "Single-copy transgenic mice with chosen-site integration."*Proc Natl Acad Sci USA* 93(17): 9067-72.

Cheng, J., A. Dutra, et al. (2004). "Improved generation of C57BL/6J mouse embryonic stem cells in a defined serum-free media." *Genesis* 39(2): 100-4.

Clapcote, S. J. and J. C. Roder (2005). "Simplex PCR assay for sex determination in mice." *Biotechniques* 38(5): 702, 704, 706.

Hogan, B., R. Beddington, et al. (1994). *Manipulating the mouse*. Cold Spring Harbor, Cold Spring Harbor Laboratory Press.

Jasin, M., M. E. Moynahan, et al. (1996). "Targeted transgenesis." *Proc Natl Acad Sci USA* 93(17): 8804-8.

Pekcec, A., W. Baumgartner, et al. (2008). "Effect of aging on neurogenesis in the canine brain." *Aging Cell* 7(3): 368-74.

Ponchio, L., L. Duma, et al. (2000). "Mitomycin C as an alternative to irradiation to inhibit the feeder layer growth in long-term culture assays." *Cytotherapy* 2(4): 281-6.

Scholzen, T. and J. Gerdes (2000). "The Ki-67 protein: from the known and the unknown." *J Cell Physiol* 182(3): 311-22.

van der Weyden, L., D. J. Adams, et al. (2002). "Tools for targeted manipulation of the mouse genome." *Physiol Genomics* 11(3): 133-64.

Young, K. A., M. L. Berry, et al. (2002). "Fierce: a new mouse deletion of Nr2e1; violent behaviour and ocular abnormalities are background-dependent." *Behav Brain Res* 132(2): 145-58.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polynucleotide comprising a MKI67 regulatory element having at least 95% sequence identity to SEQ ID NO: 3, 4 or 5 operably joined to a MKI67 basal promoter having at least 95% sequence identity to SEQ ID NO:6 through a non-native spacing of not more than 1 kb between the promoter and the regulatory element;
wherein the isolated polynucleotide can provide for a transcription rate in a cell of interest of an operably linked expressible sequence that is at least about 75% the transcription rate of the promoter sequence of SEQ ID N0:2.

2. The isolated polynucleotide of claim 1, operably linked to an expressible sequence.

3. A vector comprising the isolated polynucleotide of claim 2.

4. A cell comprising the vector of claim 3.

5. The cell of claim 4, wherein the vector is stably integrated into the genome of the cell.

6. The cell of claim 5, wherein the cell is a neuronal cell or a stem cell.

7. The isolated polynucleotide of claim 1, wherein the regulatory elements comprise a sequence having at least 95% sequence identity to SEQ ID NO: 3, a sequence having at least 95% sequence identity to SEQ ID NO:4 and a sequence having at least 95% sequence identity to SEQ ID NO:5.

8. The isolated polynucleotide of claim 1, wherein the polynucleotide has at least 95% sequence identity to SEQ ID NO:2.

* * * * *